United States Patent
Chen et al.

(10) Patent No.: US 11,879,834 B2
(45) Date of Patent: Jan. 23, 2024

(54) FLUID IDENTIFICATION USING OPTICAL DATA MEASUREMENTS

(71) Applicant: Halliburton Energy Services, Inc., Houston, TX (US)

(72) Inventors: Zhonghuan Chen, Singapore (SG); Bin Dai, Houston, TX (US); Wei Zhang, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 67 days.

(21) Appl. No.: 17/834,892

(22) Filed: Jun. 7, 2022

(65) Prior Publication Data

US 2023/0393056 A1    Dec. 7, 2023

(51) Int. Cl.
*G01N 21/27* (2006.01)
*G01N 33/24* (2006.01)
*G01N 21/85* (2006.01)

(52) U.S. Cl.
CPC ............ *G01N 21/27* (2013.01); *G01N 21/85* (2013.01); *G01N 33/241* (2013.01); *G01N 2021/8571* (2013.01)

(58) Field of Classification Search
CPC ...... G01N 21/27; G01N 21/85; G01N 33/241; G01N 2021/8571
USPC ....................................................... 356/402
See application file for complete search history.

(56) References Cited

U.S. PATENT DOCUMENTS

| | | |
|---|---|---|
| 2009/0119244 A1* | 5/2009 | Chimenti .............. G16C 60/00 706/52 |
| 2011/0108720 A1 | 5/2011 | Ford et al. |
| 2014/0360259 A1 | 12/2014 | Indo et al. |
| 2016/0177715 A1 | 6/2016 | Indo et al. |
| 2017/0261640 A1* | 9/2017 | Chen .................... E21B 47/114 |
| 2019/0360332 A1 | 11/2019 | Dai et al. |
| 2021/0071522 A1 | 3/2021 | Dai et al. |

OTHER PUBLICATIONS

Unpublished U.S. Appl. No. 17/481,165, filed Sep. 21, 2021.
(Continued)

*Primary Examiner* — Michelle M Iacoletti
*Assistant Examiner* — Omar H Nixon
(74) *Attorney, Agent, or Firm* — Kilpatrick Townsend & Stockton LLP

(57) ABSTRACT

A method includes identifying, by pre-set criteria, a first plurality of optical channels and a second plurality of optical channels using optical data generated from a plurality of optical filters of a tester tool. The method also includes determining, from the optical data, a first plurality of fluid types detected by each channel in the first plurality of optical channels using a bootstrap fluid identification technique and determining, from the optical data and the first plurality of fluid types, a second plurality of fluid types detected by each channel in the second plurality of optical channels using a guided fluid identification technique. Further, the method includes generating a spectral signature indicating fluid types for each channel within the tester tool based on the first plurality of fluid types and second plurality of fluid types.

20 Claims, 10 Drawing Sheets

(56) References Cited

OTHER PUBLICATIONS

Halliburton Energy Services, Inc., "Halliburton's Reservoir Description Tool (RDT)—RDT Focused Probe Delivers Clean Sampling Faster, with Less Sanding", product sheet available at http://hlsasia.com/wp-content/uploads/2017/10/resouviour.pdf, 2017, 2 pages.
Halliburton Energy Services, Inc., International Search Report and Written Opinion, PCT/US2022/032580, dated Feb. 21, 2023, 9 pages.

* cited by examiner

FLUID IDENTIFICATION USING OPTICAL DATA MEASUREMENTS

TECHNICAL FIELD

The present disclosure relates generally to wellbore drilling operations and, more particularly (although not necessarily exclusively), to identifying fluid types in subsurface fluid flows using optical data measurements.

BACKGROUND

Within a wellbore, a reservoir tester tool can sample formation fluids and extract optical signatures to analyze the composition of the formation fluids. Multiphase fluid flow may be present due to fluid contamination from mud filtrate. The formation fluids may be observed in some optical channels, while the mud filtrate may be observed in others. In this manner, optical measurements using the reservoir tester tool may not include pure formation spectral signatures, and the optical signatures for the formation fluid may not be isolated from the observed multiphase fluid flow.

DETAILED DESCRIPTION

Figure 1:
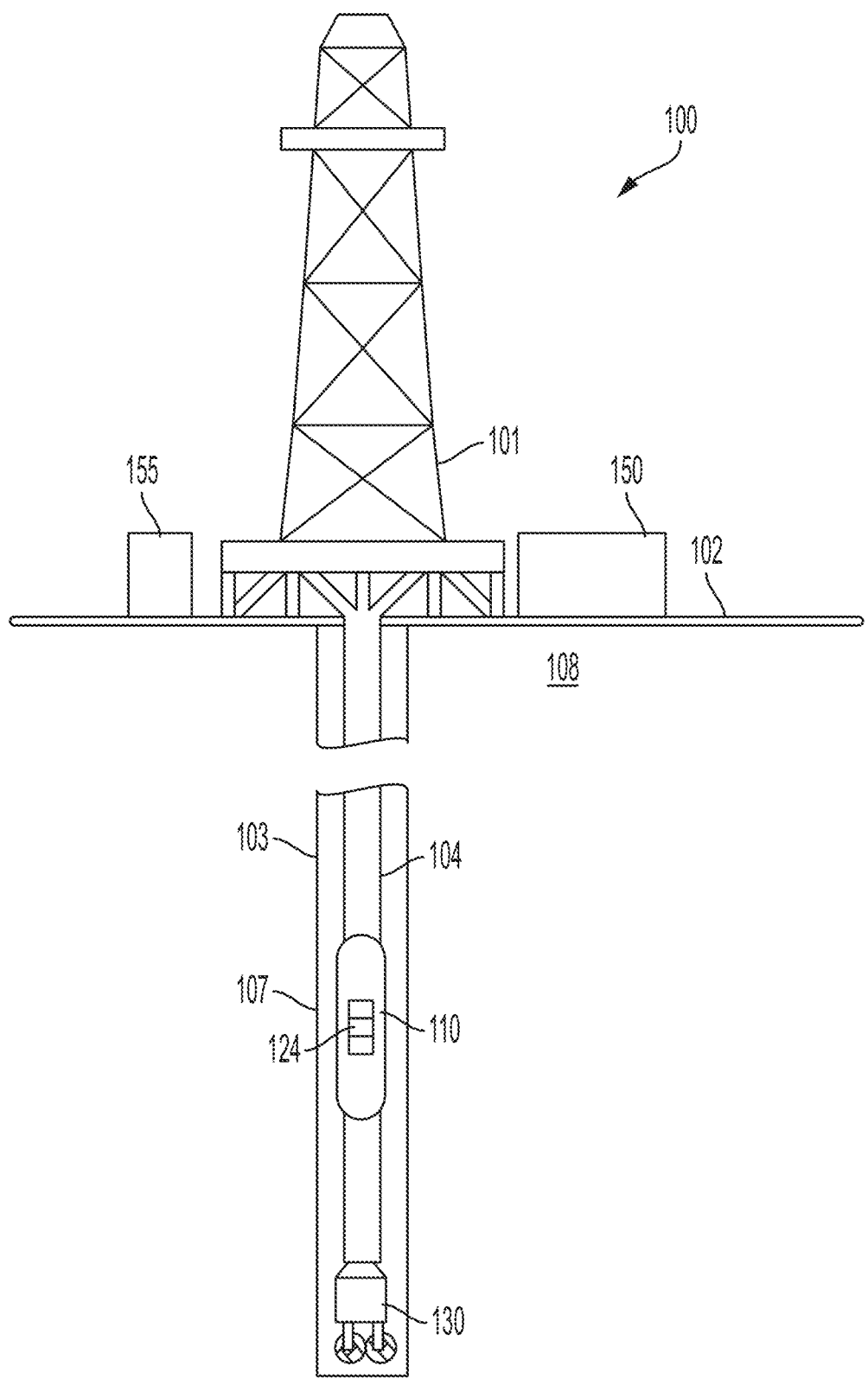
FIG. 1 is a diagram of a drilling rig for drilling a wellbore into a subterranean formation according to one example of the present disclosure.

Certain aspects and examples of the present disclosure relate to identifying fluid types in subsurface fluid flows using optical data measurements. In an example, optical filters can collect optical data and form one or more optical channels for use in optical data measurement. Optical filters can be positioned in a formation tester tool that is used to measure physical characteristics within a wellbore. For an example, stable and sensitive optical channels can be selected from all other optical channels of the optical filters using the optical data generated from optical filters. The stable and sensitive optical channels can be used to determine the first fluid types by adopting a bootstrap fluid identification technique. The bootstrap fluid identification technique can be a technique that uses readings from optical channels that are recognized as stable and sensitive to light energy based on laboratory analysis. A sensitivity of an optical channel may be determined based on a determination of whether the light energy received at a light sensor from the selected filters distributes the formation fluids and the mud filtrate separately based on pre-set laboratory parameters. A stability of the optical channel may be determined based on a determination of whether the light energy received at a light sensor from the selected filter indicating the formation fluids is stronger than the light energy indicating the mud filtrate or whether the light energy received at the light sensor from the selected filter indicating the mud filtrate is stronger than the light energy indicating the formation fluids, based on pre-set laboratory parameters. However, the bootstrap fluid identification technique optical channels cannot be utilized when the optical channels are not considered stable and sensitive because the light energy from these filters cannot be distributed separately or distinguish formation fluids from mud filtrate. Therefore, all optical channels may be grouped into two groups. The first group of optical channels may represent stable and sensitive optical channels, while the second group of optical channels may represent all other optical channels. In some examples, the fluids in the first group of optical channels can be identified as mud filtrate or formation fluids. With the identified fluid types and stationary statistics from the optical channels in the first group, the fluid types of optical channels in the second group can be identified.

For example, a fluid ratio, as one type of stationary statistic, can be generated from the first group as guided information. In this case, the guided information can be used as reference information to predict fluid types in other optical channels that are sampled within a similar time interval. In an example, stationary statistics can refer to the mathematical statistics or relationship that the statistical properties of a process that generates a time series do not change over time. In other words, the series does not change over time. Thus, stationary statistics represented as an algebraic equivalent is a linear function. For example, the value of a linear function changes as x increases, and the slope remains constant. The stationary statistics can be involved in determining the second group for all other optical channels with the optical data. Further, with fluids in both the first and second groups identified, we can generate the spectral signatures for both the formation fluids and mud filtrate. These signatures can be used in composition analysis for the fluids and further drilling operations in the wellbore.

In some examples, a multiphase analysis method may be used as guide information from physical measurements other than optical measurements, such as density or capacitance. A multiphase analysis method may involve analysis of multiphase fluid. The term "multiphase fluid" may refer to the simultaneous flow of more than one type of fluid phase through a porous medium in a wellbore. Thus, the wellbore may produce both oil and gas from multiphase fluid, such as formation fluid and mud filtrate. The multiphase fluid flow analysis can simulate the interaction between two fluid phases and their behavior. The analysis can be carried out using the Volume of Fluid (VoF) method, which is a method for calculating multiphase systems. The spectral signature can work properly when the guide information is sufficient and accurate.

In some examples of the present disclosure, the guided information may occur based on a bootstrap fluid identification technique and a guided fluid identification technique. The bootstrap fluid identification technique may be used for the optical channels that are relatively sensitive when light energy is transmitted through the selected optical channels in a manner that detects the distribution of formation fluids and mud filtrate separately. The bootstrap fluid identification technique may also be used for the optical channels that are relatively stable optical channels may when the light energy is transmitted through the selected optical channels in a manner that detects the formation fluids more strongly than the mud filtrate or in a manner that detects the mud filtrate more strongly than the formation fluids. In one example, stable and sensitive optical channels can be identified directly based on the pre-set criteria or other laboratory parameters. For other optical channels that are not as stable and sensitive as the stable and sensitive, the guided fluid identification technique can be adopted by using an accumulated fluid ratio as guided information to predict fluid types. The accumulated fluid ratio can be the statistical variable related to historical information about measured fluid overall sampling periods.

Illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 is a diagram of a drilling rig for drilling a wellbore into a subterranean formation according to one example of the present disclosure. In FIG. 1, a drilling system 100 may include a drilling rig 101 located at the surface 102 of a borehole 103. The drilling system 100 may also include a pump 150 that can be operated to pump mud through a drill string 104. The drill string 104 can be operated for drilling the borehole 103 through the subsurface formation 108 using the drill bit 130.

The drilling system 100 may include a formation tester tool 110 to acquire sensor channel measurements from fluid and fluid mixtures in the borehole, such as a pure formation fluid, a pure drilling fluid, a mixture of formation fluid and drilling fluid, etc. The formation tester tool 110 can be part of the drill string 104 and lowered into the borehole, optionally as part of a bottom hole assembly. The formation tester tool 110 can sample a formation fluid (e.g., draw formation fluid into the formation tester tool 110 from the subsurface formation 108) or a mixture that can include the formation fluid to acquire sensor measurements. The formation tester tool 110 in this example can include a set of probes 124 for drawing formation fluid and transfer the formation fluid to a set of sensors of the formation tester tool 110 for measurement. The set of sensors can acquire the sensor channel measurements that can detect at least one attribute of the mixture of formation fluid and drilling fluid. The set of sensors on the formation tester tool 110 can include optical sensors, resistivity sensors, viscosity sensors, density sensors, pressure sensors, or any other sensors capable of detecting at least one attribute of the mixture of formation fluid and drilling fluid. For example, the set of sensors can include an optical sensor that detects multiple sensor channel measurements as the formation tester tool 110 is lowered into the formation. These channel measurements can be collected over time to generate time-series measurements. During drilling, mud from the pump 150 can mix with formation fluids flowing into the well 103 from the formation wall 107.

During or after the set of sensors acquire sensor channel measurements, the computer 155 can use the sensor channel measurements to generate optical data. The computer 155 can also process the optical data to determine a prediction curve and associated end members. The computer 155 can also predict pure formation fluid properties, characterize the pure formation fluid coming out of the formation wall 107, or perform a combination thereof. Moreover, in response to determining that a pure formation fluid is either not present or does not contain sufficient quantities of one or more target fluids, drilling operations can be altered or stopped. These operations are further described below.

Figure 2:
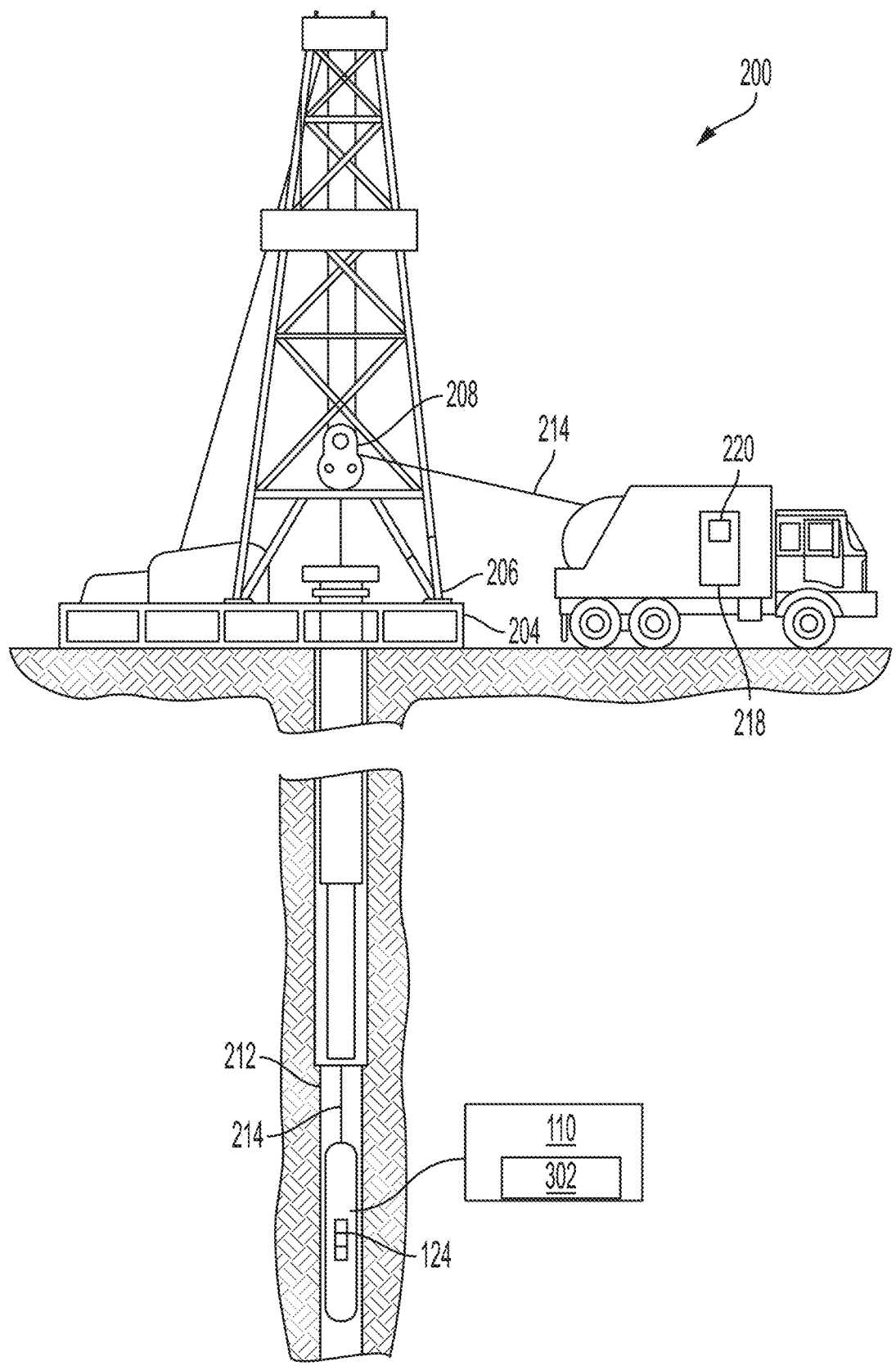
FIG. 2 is a diagram of an onshore platform operating a wireline tool within a wellbore according to one example of the present disclosure.

In an example, instead of an onshore platform operating a downhole drilling assembly with the formation tester tool 110, the formation tester tool 110 can be a wireline tool. FIG. 2 is a diagram of an onshore platform operating a wireline tool within a wellbore according to one example of the present disclosure. The onshore platform 200 includes a drilling platform 204 installed over a borehole 212. The drilling platform 204 is equipped with a derrick 206 that supports a hoist 208. The hoist 208 supports the formation tester tool 110 using a conveyance 214. Specific examples of the conveyance 214 can be a slickline, coiled tubing, piping, a downhole tractor, or a combination thereof. The formation tester tool 110 can be lowered by the conveyance 214 into the borehole 212. The formation tester tool 110 may be lowered to the bottom of the region of interest and subsequently pulled upward at a substantially constant speed.

The formation tester tool 110 is suspended in the borehole by the conveyance 214 that connects the formation tester tool 110 to a surface system 218 (which can also include a display 220). In some examples, the formation tester tool 110 can include a set of probes 124, analogous to the set of probes 124 described in FIG. 1. The set of probes 124 can be employed to draw formation fluid and provide the formation fluid to a set of sensors. The set of sensors acquires sensor channel measurements that can be used to measure formation fluid properties. The sensor channel measurements can be communicated to a surface system 218 via the conveyance 214 for storage, processing, and analysis. The formation tester tool 110 can be deployed in the borehole 212 on coiled tubing, jointed drill pipe, hard-wired drill pipe, or any other suitable deployment technique. In some examples, the conveyance 214 can include sensors to acquire sensor channel measurements. The surface system 218 can perform similarly to the computer 155 in FIG. 1 and generate fluid property predictions based on the optical data. While described as being performed by the computer 155 or the surface system 218 at the surface, some or all of these operations can be performed downhole or at a location that is remote to the drilling site.

Figure 3:
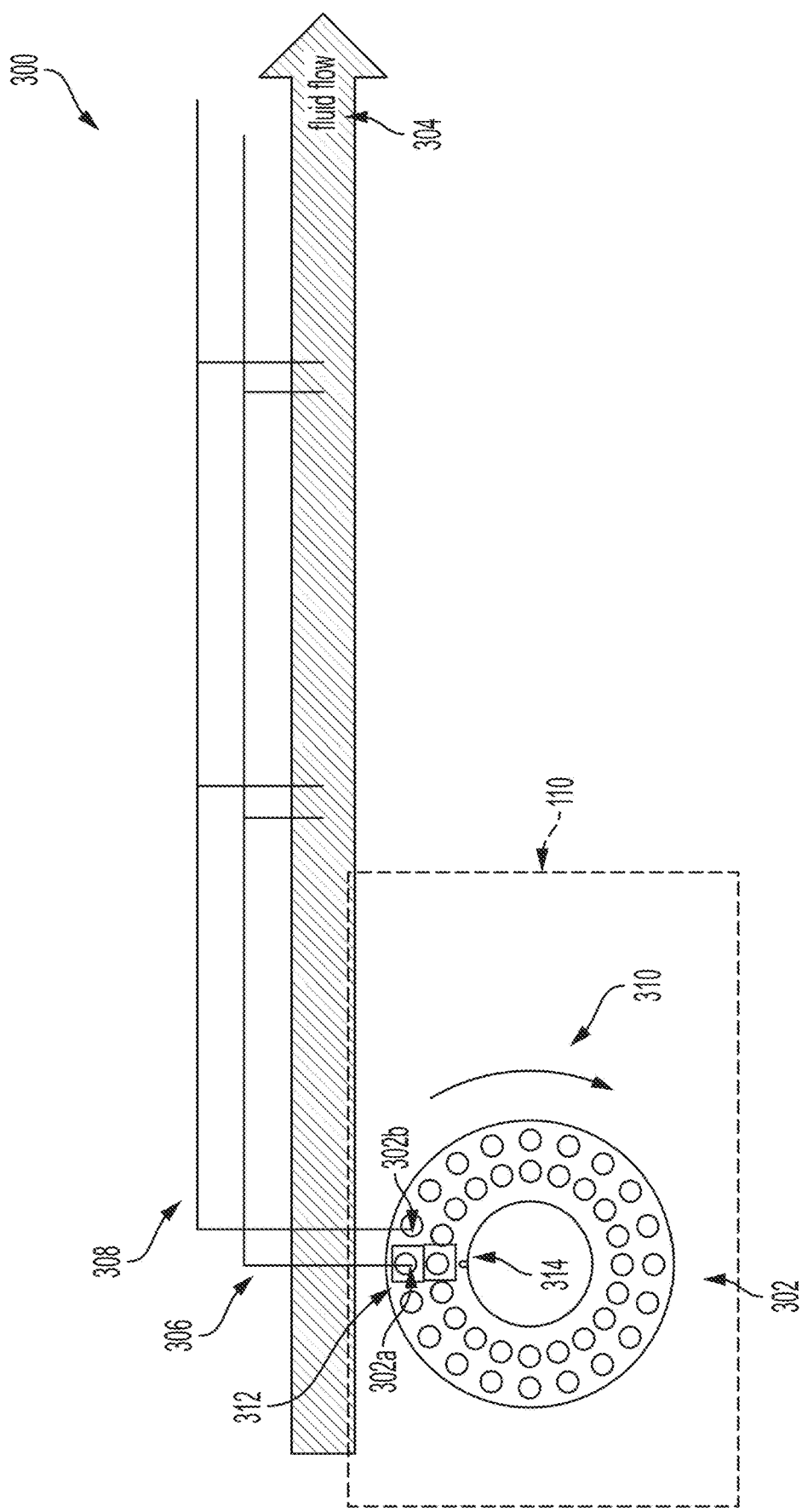
FIG. 3 is a diagram of an example of a reservoir tester measuring optical energy for each optical channel of the reservoir tester in a sub-sampling process according to one example of the present disclosure.

FIG. 3 is a diagram of an example of measuring optical energy for each optical channel in a sub-sampling process 300 according to one example of the present disclosure. In a certain example, the measured optical light energies from a first set of optical channels can be used as stationary statistics to determine fluids for the rest of the optical channels. Plural optical filters 302 of the formation tester tool 110 can be deployed within the borehole 103 within the subsurface formation 108. For example, the light can pass through the plural optical filters 302 via the fluid flow 304

(e.g., mud filtrate and formation fluids). The fluid flow 304 can include formation fluid and mud filtrate or other fluid contained in the fluid flow, such as hydraulic fluid. The plural optical filters 302 can be used to measure light energy transmitted through the fluid flow (e.g., through the formation fluid and the mud filtrate). Once the light energies are measured by the tester tool 110 using the plural optical filters 302, the light energies can be used as optical data for further use in identifying fluid types of fluid in the fluid flow 304.

In one example, a sampling cycle of the plural optical filters 302 can be arranged in a single-ring configuration or a dual-ring configuration, as shown, for measuring and receiving the optical data from the fluid flow 304. In one implementation, more than one optical channel can be deployed on the plural optical filters 302 for the fluid flow 304 passing through and being measured in light energy. Each optical channel may receive and measure different light energy samples of the fluid flow 304. For example, one optical channel 302a may receive the first sample of light energy traversing a fluid 306 from the fluid flow 304. Whereas another optical channel 302b positioned adjacent to the optical channel 302a may receive a second sample of light energy traversing a fluid 308 from the fluid flow 304.

In one example, by rotating 310 the plural optical filters 302, each optical channel can sample light energy from certain portions of the fluid flow 304 through a sensor positioned in the plural optical filters 302 as time progresses. In another example, the plural optical filters 302 can include a two-ring arrangement, as shown in FIG. 3. For example, an outer ring of the plural optical filters 302 can have a first sensor 312, and an inner ring of the plural optical filters 302 can have a second sensor 314. Both sensors 312 and 314 can simultaneously sample light energy from the fluid flow 304 at a corresponding ring. The rotation 310 of the plural optical filters 302 can proceed in a clockwise direction, as shown in FIG. 3, for sampling light energy from different parts of the fluid flow 304 through each optical channel in the plural optical filters 302. In an additional example, the rotation 310 of the plural optical filters 302 can proceed counterclockwise. When either sensor 312 or 314 samples the light energy of the fluid flow 304 at the last channel in either a clockwise direction or counterclockwise direction, then the light energy measurements taken by the plural optical filters 302 can be considered a complete sampling cycle of the tester tool 110. To complete a sampling cycle may take 10 seconds for the test tool 110, but the tester tool 110 may take more or less time to complete a sampling cycle in some examples. Various arrangements of the plural optical filters 302 can be provided depending on the specific applications, and the arrangement described herein should not be considered limiting.

In some examples, the plural optical filters 302 can be designed and positioned on or in the tester tool 110 before measuring optical data from the fluid flow 304. Due to the different absorbing wavelengths of fluid compositions of the fluid flow 304, the plural optical filters 302 may include one or more transfer functions for corresponding optical channels to identify fluid types from the fluid flow 304. The following equation (1) can be used to calculate light energy for each optical channel on the plural optical filters 302 of the tester tool 110:

$$d_i = \int T(\lambda) f_i(\lambda) d\lambda, \quad (1)$$

where $d_i$ is an observed optical light energy for an i-th optical channel of the plural optical filters 302, $f_i(\lambda)$ is a transfer function for the i-th optical channel on the plural optical filters 302, and $T(\lambda)$ is a light transmitting spectrum through the samples of the fluid flow 304 on the wavelength $\lambda$. Mathematically, the fluid identification problem is to determine whether the transmitting spectrum $T(\lambda)$ comes from the mud filtrate or the formation fluids.

Figure 4:
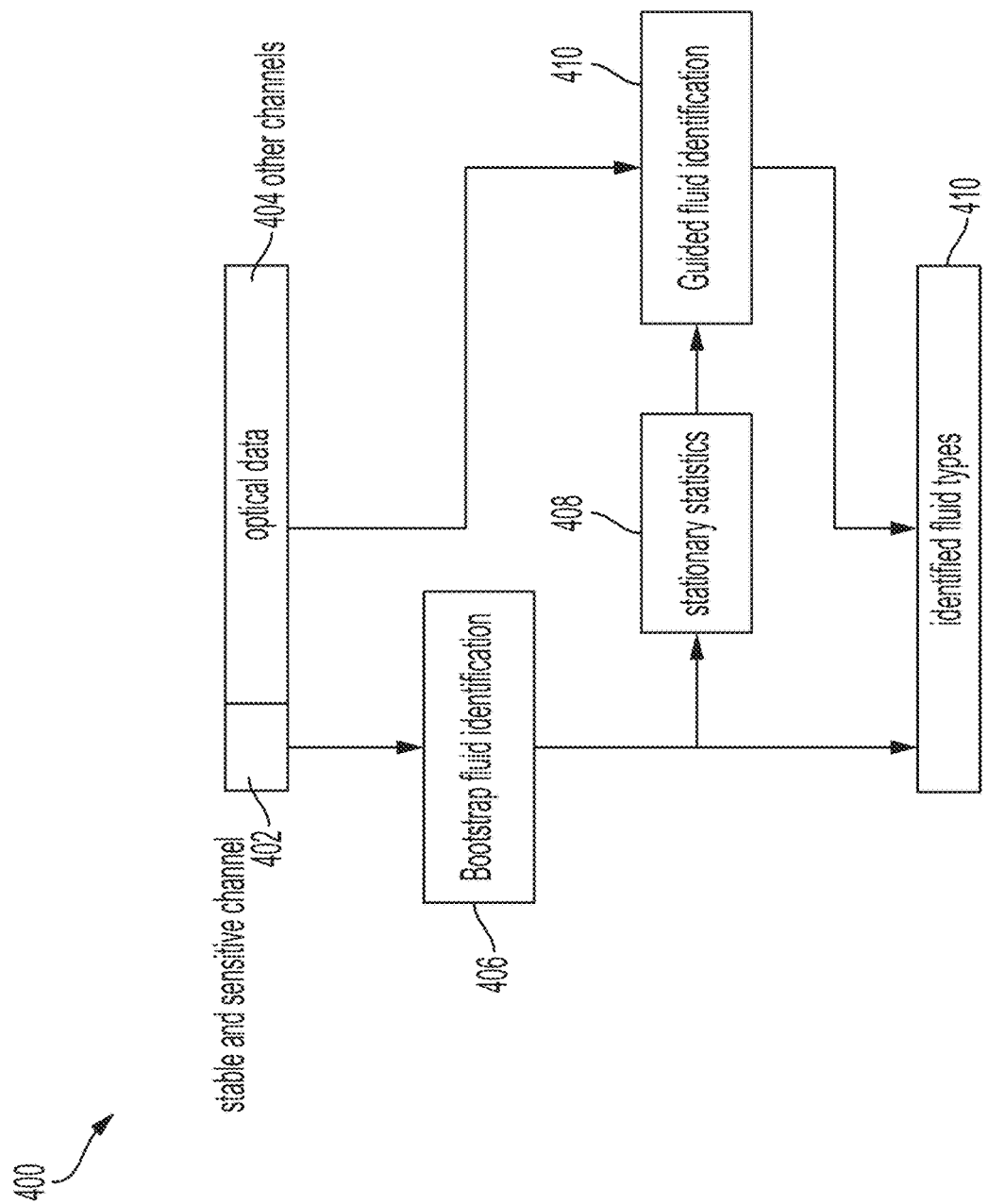
FIG. 4 is a diagram of identifying fluid types using a bootstrap technique and a guided identification technique according to one example of the present disclosure.

FIG. 4 is a diagram 400 of identifying fluid types using a bootstrap technique and a guided identification technique according to one example of the present disclosure. For example, all optical channels can be grouped into two groups, including stable and sensitive channels 402 and other channels 404 by determining which optical channels provide stable and sensitive measurements. As described previously, sensitive optical channels may be identified based on whether the light energy detected through the formation fluids and the mud filtrate by the selected filters distributes separately based on pre-setting laboratory parameters. Further, the stable optical channels may be identified based on whether the light energy detected by the selected filter through the formation fluids is stronger than the light energy detected through the mud filtrates, or vice versa, based on pre-setting laboratory parameters.

A bootstrap fluid identification technique 406 can be employed to identify fluid types 410 of the stable and sensitive channels 402. In other words, because the channels 402 are stable and sensitive, the light energy readings from the channels 402 may be used directly to determine the fluid types. Further, using the identified fluid types 410 of the stable and sensitive channels 402, stationary statistics 408 can be generated, such as an accumulated fluid radio, to provide guidance for a guided fluid identification technique 410 that is used to determine fluid types for other channels 404. With the combined bootstrap fluid identification technique 406 and the guided fluid identification technique 410, all fluid types can be identified for all optical channels of the tester tool 110.

Figure 5:
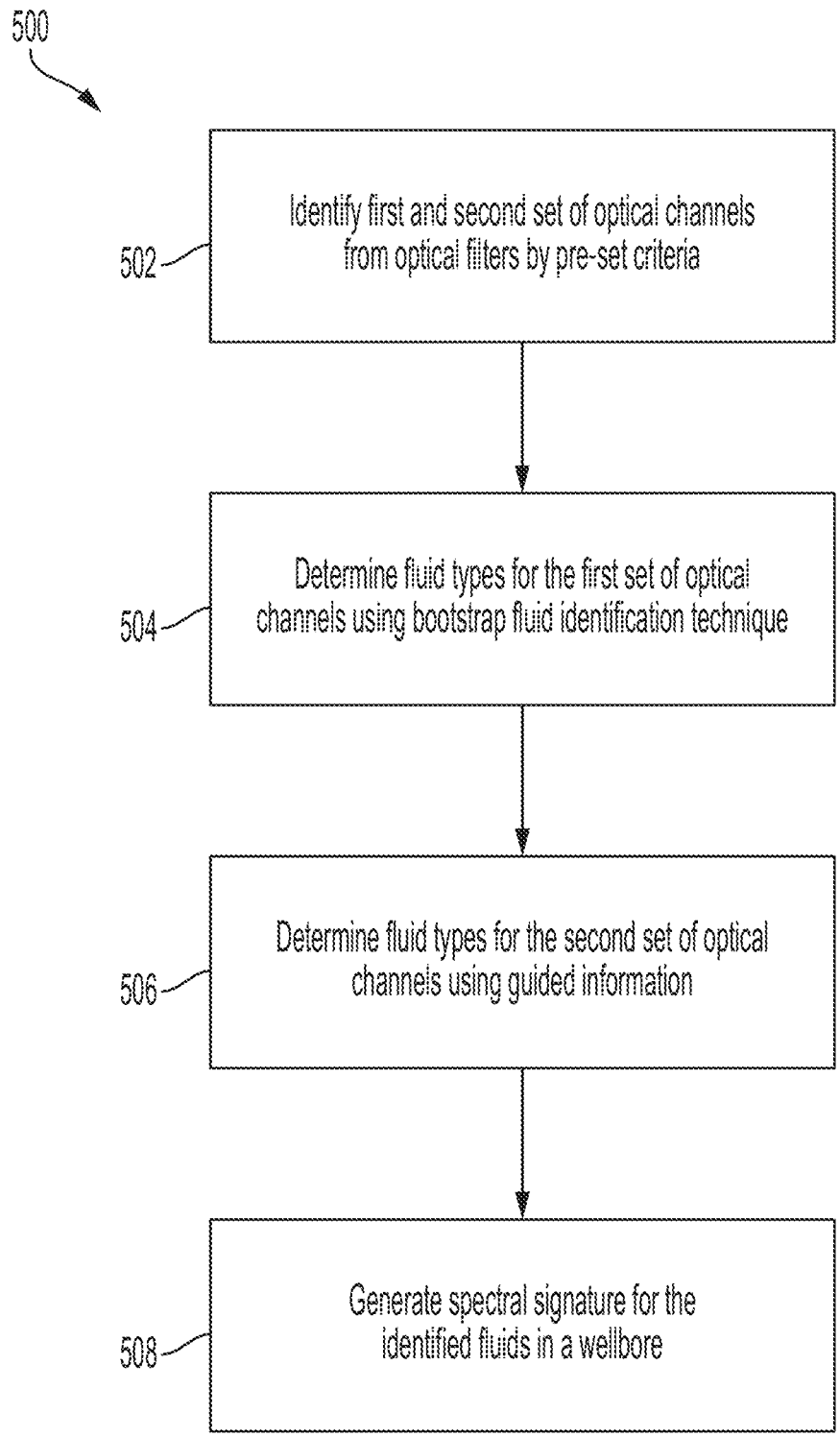
FIG. 5 is a flowchart of a process for identifying the subsurface fluid of a wellbore according to one example of the present disclosure.

FIG. 5 is a flowchart of an example of a process 500 for identifying subsurface fluid from a wellbore according to one example of the present disclosure. The process 500 may be implemented in software (e.g., code, instructions, program) executed by one or more processing units (e.g., processors, cores) of the respective systems, hardware, or combinations thereof. The software may be stored on a non-transitory storage medium (e.g., on a memory device). The process 500 presented in FIG. 5 and described below, is intended to be illustrative and non-limiting. Although FIG. 5 depicts the various processing blocks occurring in a particular sequence or order, this is not intended to be limiting. In certain alternative embodiments, the blocks may be performed in some different order or some blocks may also be performed in parallel.

The process 500 can be implemented in software executed by processors of the system or hardware to receive the optical data measured from the plural optical filters 302. At block 502, the process 500 can identify the first set of optical channels and the second set of optical channels from a set of optical filters. Each filter in the set of optical filters can form an optical channel for light energy transmitted through formation fluid or mud filtrate to pass. In one example, the set of optical filters can be the plural optical filters 302 described in FIG. 3. The process 500 can identify the first set of optical channels and the second set of optical channels from the set of optical filters based on pre-set criteria. The pre-set criteria can be used to evaluate each channel from the set of optical filters in terms of sensitivities and stabilities using the optical data. The most sensitive and stable optical channels can be selected from the set of optical filters as the first set of optical channels, and all other optical channels can be identified as the second set of optical channels.

Additionally, or alternatively, the first set of optical channels can be used to determine the fluid types by themselves since the first set of optical channels are considered as stable and sensitive channels, as described previously. Moreover, the fluid types of the first set of optical channels can be used to guide the determination of the fluid types for the second set of optical channels in the following blocks.

In one implementation, and referring to components of equation (1), the pre-set criteria can include the pre-setting laboratory parameters related to filling pure nitrogen in the sampling path for each optical channel to measure the corresponding transfer functions $f_i(\lambda)$. The transmitting spectra $T(\lambda)$ of some common oil and gas samples and mud filtrate can then be observed. To ensure stability, the transmitting spectrum $T(\lambda)$ for each fluid flow sample can also be measured in different temperature and pressure conditions. Thus, using the different transfer functions $f_i(\lambda)$ and measured transmitting spectrum $T(\lambda)$, the optical light energy $d_i$ can be calculated. Once the optical light energy $d_i$ is calculated, the first set of optical channels can be identified by selecting the optical channels with optical light energy $d_i$ that distributes separately and distinguishes formation fluids from mud filtrates based on pre-setting laboratory parameters. After the stable and sensitive optical channels are selected as the first set of optical channels, all of the other optical channels of the tester tool 110 can be considered the second set of optical channels.

Figure 6:
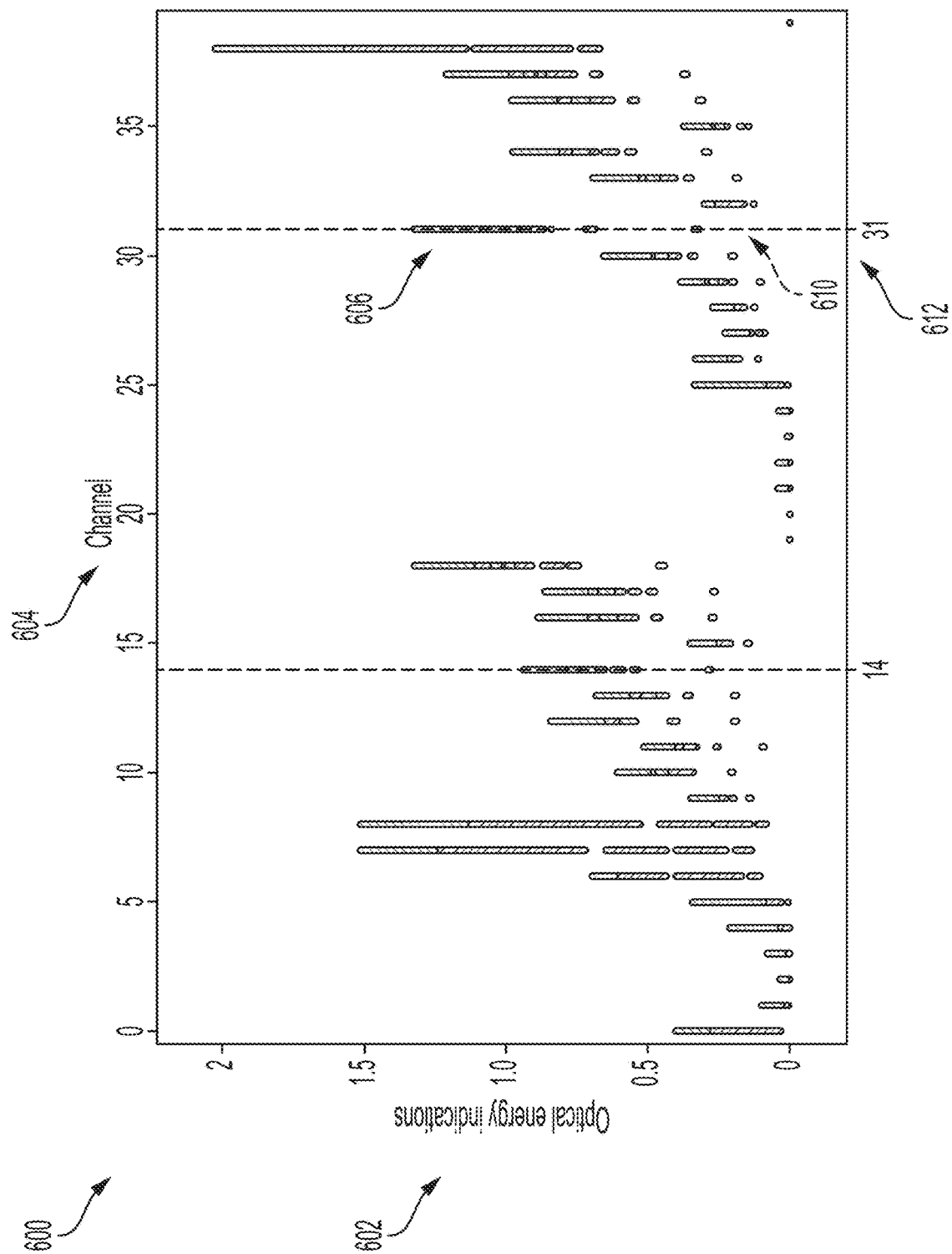
FIG. 6 is a diagram of distributed optical energy with corresponding optical channels according to one example of the present disclosure.

To help illustrate the optical light energy $d_i$ for the set of optical channels, FIG. 6 is a diagram 600 of distributed optical energy with corresponding optical channels according to one example of the present disclosure. In some examples, the optical light energies $d_i$ detected at each of the optical channels 604 are shown in optical energy indications 602. For example, the optical channel 31 has a depiction of a detected energy indication 612, where groups 606 and 610 represent various energy density levels over the energy indication 612. By observing the distribution of groups 606 and 610, the stability and sensitivity can be determined based on the pre-set criteria. As illustrated, the optical channels 0-4, 6-8, 19-24, 38, and 39 have energy indications 612 of mud filtrate overlapped with hydrocarbons. This overlapping may indicate that mud filtrate in the above optical channels may have stronger optical light energy $d_i$ responses than the hydrocarbons in some cases but weaker in other cases based on the pre-set criteria. Thus, optical channels 0-4, 6-8, 19-24, 38, and 39 may not be considered stable. On optical channels 5, 9-18, and 25-37, mud filtrate has weaker optical light energy responses than hydrocarbons in all cases based on the pre-set criteria. Thus, optical channels 5, 9-18, and 25-37 may be considered stable. Among all these stable optical channels, optical channels 14, 18, 31, and 34 may provide more sensitivity than the other stable optical channels. As shown, the two most sensitive and stable optical channels are optical channels 31 and 14. Therefore, the optical channels 31 and 14 may be identified as the first set of optical channels, and all other optical channels can be identified as the second set of optical channels. While two optical channels are described in FIG. 6 as being included in the first set of optical channels, more or fewer optical channels may be used in the first set of optical channels depending on the levels of stability and sensitivity expressed by those channels.

Referring back to FIG. 5, at block 504, the process 500 can be implemented in software executed by processors of system or hardware to determine the fluid types for the first set of optical channels using the bootstrap fluid identification technique. In one example, the bootstrap fluid identification technique can be used to determine fluid types for the first set of optical channels, which can be stable and sensitive optical channels described in FIG. 6 using only the optical data. By doing so, the fluid types of the first set of optical channels can be used as guided information for use in determining the fluid types for the second set of optical channels using a bootstrap fluid identification technique.

At block 506, the process 500 can be implemented in software executed by processors of system or hardware to determine the second fluid types for the second set of optical channels by using stationary statistics as guided information. In some examples, the stationary statistics can be generated from the bootstrap fluid identification technique described in block 504. In other examples, the stationary statistics can include an accumulated formation fluid ratio, an accumulated formation fluid density, and an accumulated formation fluid capacitance. For example, upon determining the fluid types from the first set of optical channels, the accumulated formation fluid density and capacitance can be measured based on the fluid properties of the fluid types.

At block 508, the process 500 can be implemented in software executed by processors of system or hardware to generate a spectral signature based on the identified fluid types of the first and second sets of optical channels. In some examples, the spectral signature can be used to predict fluid properties and composition of fluid flows in the subsurface and the formation of the wellbore. Also, the spectral signature can be used to predict fracking geometries to further identify locations of fluid flows in the subsurface and fluid flow compositions. In some examples, by knowing the locations of fluid flows in the subsurface and the fluid compositions, the drilling operations can aim toward certain areas in the formation containing fluid flows where the formation fluid ratio indicates a significant prevalence of hydrocarbons. The accumulated formation fluid ratio can be the ratio of pure formation to mud filtrate based on fluid flow compositions. As such, drilling operations or other operations in the wellbore can perform effectively by avoiding areas with undesired accumulated formation fluid ratio of fluid flows in the subsurface of the wellbore. Therefore, Identifying the subsurface fluid using the spectral signature can be enhanced the successful performance of drilling operations and other operations.

Figure 7:
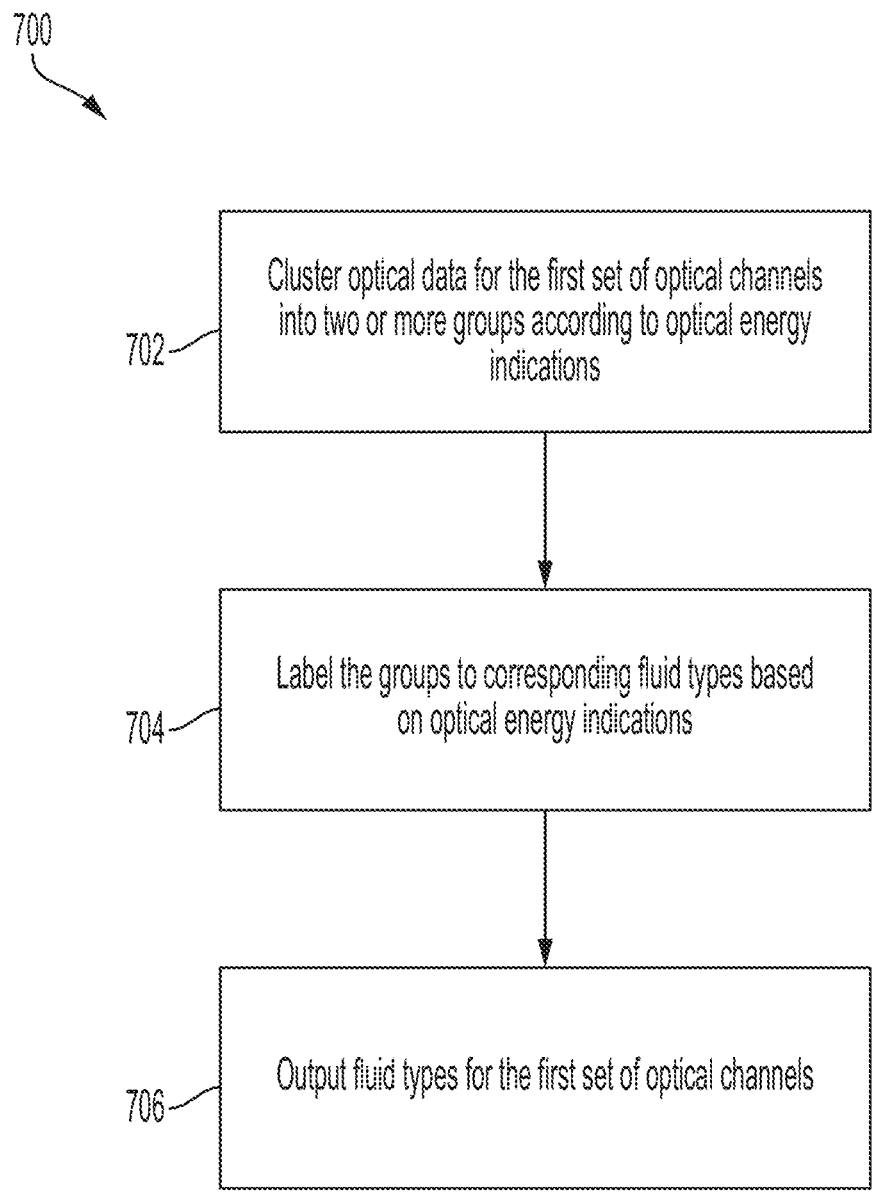
FIG. 7 is a flowchart of an example of a process for determining fluid types of the first set of optical channels according to one example of the present disclosure.

FIG. 7 is a flowchart of an example of a process 700 for determining the fluid types of the first set of optical channels according to one example of the present disclosure. The process 700 may be implemented in software (e.g., code, instructions, program) executed by one or more processing units (e.g., processors, cores) of the respective systems, hardware, or combinations thereof. The software may be stored on a non-transitory storage medium (e.g., on a memory device). The process 700 presented in FIG. 7 and described below is intended to be illustrative and non-limiting. Although FIG. 7 depicts the various processing blocks occurring in a particular sequence or order, this is not intended to be limiting. In certain alternative embodiments, the blocks may be performed in some different order, or some blocks may also be performed in parallel.

At block 702, the process 700 can be implemented in software executed by processors of system or hardware to cluster the optical data for the first set of optical channels into at least two groups based on the optical energy indications 602 described in FIG. 6 from the optical data. Additionally, or alternatively, the first set of optical channels can be grouped based on the pre-set criteria with the optical energy indications 602.

At block 704, the process 700 involves labeling each group as a particular fluid type based on the optical energy indications from the optical data. Referring back to FIG. 6, the optical energy indications in the diagram 600 can indicate a fluid type for each group. For example, on the optical channel 34, the first group 606 on the optical channel 34 has the highest optical energy response, so the first group 606 may be labeled as a hydrocarbon fluid. The second group 610 on the optical channel 34 has a lower optical energy response, so the second group 510 may be labelled as mud filtrate.

At block 706, the process 700 involves the tester tool 110 outputting the fluid types of the first set of optical channels (e.g., from the stable and sensitive optical channels) to the computer 155.

Figure 8:
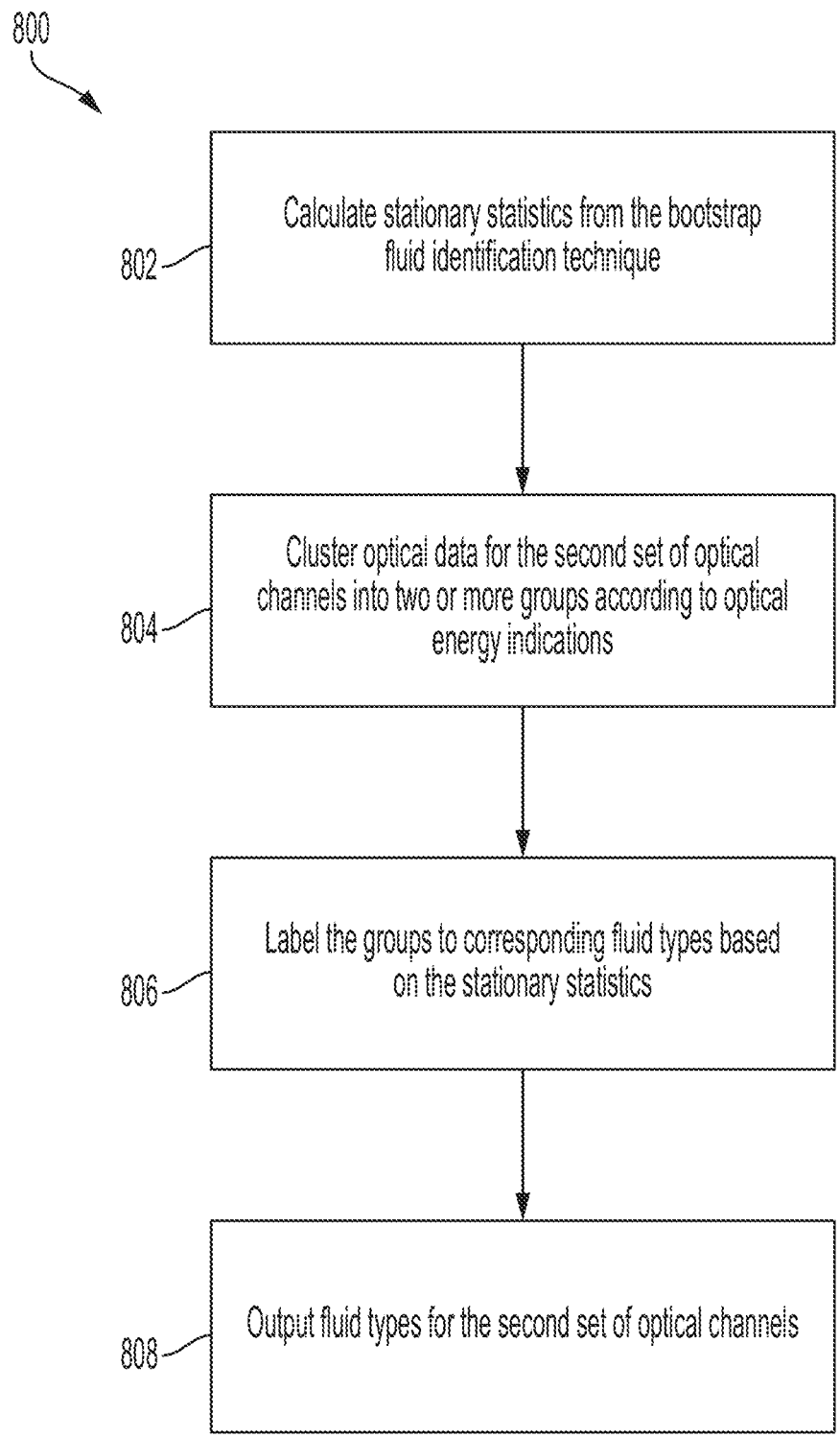
FIG. 8 is a flowchart of a process for determining fluid types of the second set of optical channels according to one example of the present disclosure.

FIG. 8 is a flowchart of an example of a process 800 for determining the fluid types of the second set of optical channels according to one example of the present disclosure. The process 800 may be implemented in software (e.g., code, instructions, program) executed by one or more processing units (e.g., processors, cores) of the respective systems, hardware, or combinations thereof. The software may be stored on a non-transitory storage medium (e.g., on a memory device). The process 800 is presented in FIG. 8 and described below are intended to be illustrative and non-limiting. Although FIG. 8 depicts the various processing blocks occurring in a particular sequence or order, this is not intended to be limiting. In certain alternative embodiments, the blocks may be performed in some different order, or some blocks may also be performed in parallel.

At block 802, the process 800 can be implemented in software executed by processors of system or hardware to calculate the stationary statistics from the bootstrap fluid identification technique described in block 504. After determining the fluid types for the first set of optical channels, as described in block 504, the accumulated formation fluid ratio can be known. In some examples, the accumulated formation fluid ratio can be used as one of the stationary statistics in determining the fluid types for the second set of optical channels.

At block 804, the process 800 involves clustering the second set of optical channels into at least two groups based on the optical energy indications 602 described in FIG. 6 from the optical data. Additionally, or alternatively, the second set of optical channels can be grouped based on the pre-set criteria with the optical energy indications 602.

At block 806, the process 800 involves labeling based on the stationary statistics generated from the bootstrap fluid identification technique. In one implementation of determining the fluid types of the second set of channels, as described above, the fluid types of the first set of channels may be identified using the bootstrap fluid identification technique, and the fluid types of the first set of optical channels are used as the guided information to determine the fluid types for the second set of optical channels. In one example, the identified fluid types of the first set of optical channels can be used to generate stationary statistics. The stationary statistics can be used as the guided information.

The stationary statistics can include an accumulated formation fluid ratio, an accumulated formation fluid density, and an accumulated formation fluid capacitance. In certain implementations, a certain optical channel in the first set of optical channels can have a similar accumulated formation fluid ratio with another optical channel in the second set of optical channels nearby within the same tester tool 110. Thus, using the accumulated formation fluid ratio from the identified fluid types of optical channels can refer to the similar accumulated formation fluid ratio for the later optical channels. With the known fluid types and the known accumulated formation fluid ratio, the fluid types of the later optical channels can be derived by referring to the identified fluid types of the nearby optical channel because they have similar accumulated formation fluid ratios.

For example, the accumulated formation fluid ratio with the corresponding fluid types from a particular optical channel in the first set of optical channels may include 70% hydrocarbons and 30% mud filtrate. An optical channel in the second set of optical channels that is physically near the particular optical channel of the tester tool 110 may have a similar accumulated formation fluid ratio (i.e., 70% hydrocarbons and 30% mud filtrate) based on the optical energy indications. The fluid types may still be unknown for the optical channel in the second set of optical channels. By referring to the first fluid types of the optical channel in the first set of optical channels, the fluid types of the optical channel in the second set of optical channels may be predicted since they should have a similar accumulated formation fluid ratio. As such, the fluid types of the optical channel of the second set of optical channels can also be labeled as 70% hydrocarbons and 30% of mud filtrate.

At block 808, the process 800 involves the tester tool 110 outputting the fluid types of the second set of optical channels to the computer 155. In some examples, the fluid types of types of the second set of optical channels can further be used to generate a fluid spectral signature.

Figure 9:
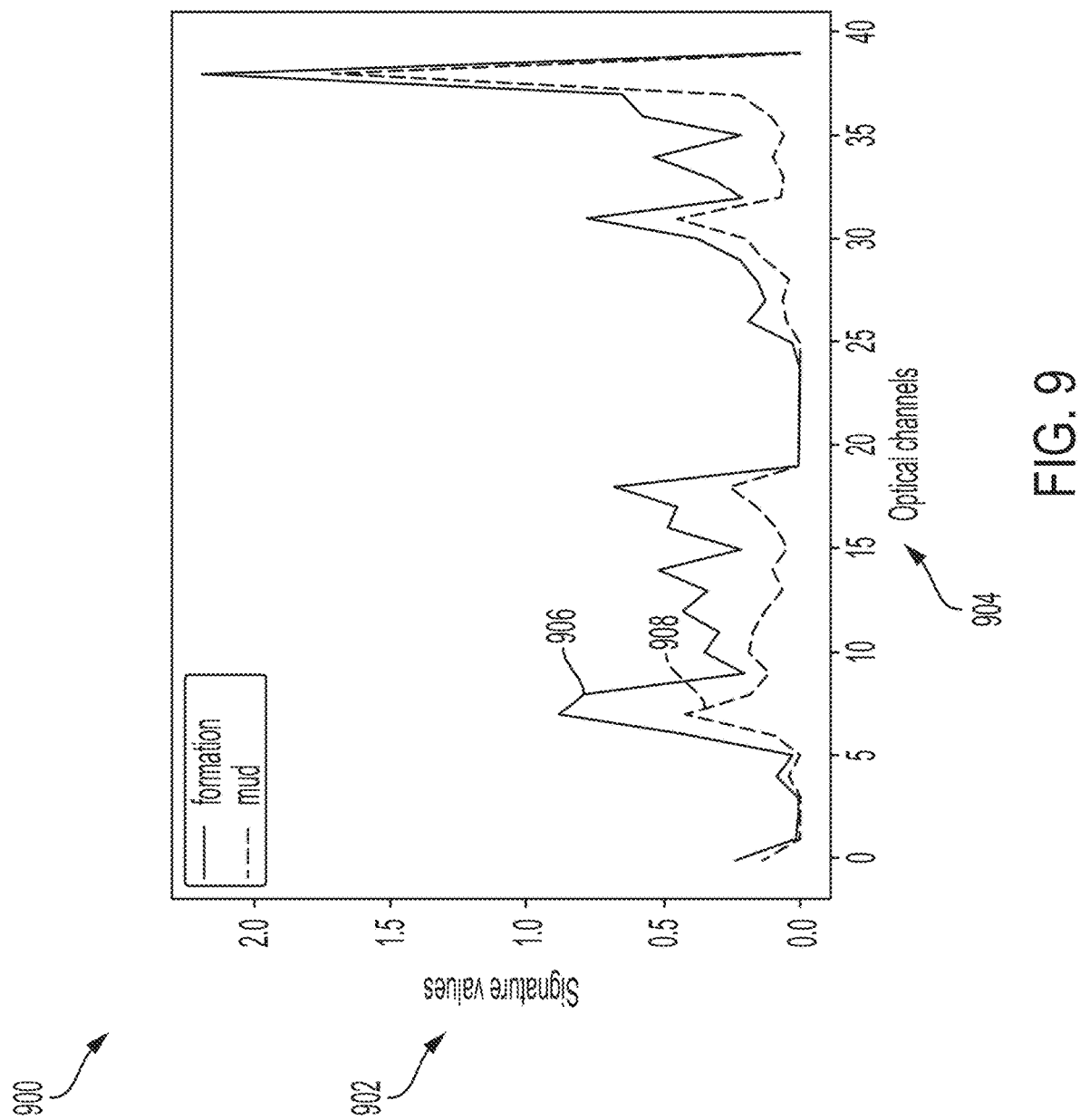
FIG. 9 is a diagram of an example of generating a spectral signature using each optical channel according to one example of the present disclosure.

FIG. 9 is a diagram 900 of an example of spectral signatures of formation fluid and mud filtrate at a point in time according to one example of the present disclosure. Through the processes 500, 700, and 800 discussed above with respect to FIGS. 5, 7, and 8, the fluid types can be determined from the optical data for all optical channels on the plural optical filters 302. In one example, the fluid types of the first and second set of optical channels can be stored for use in generating a fluid spectral signature. With the fluid types of the first and second sets of optical channels, a fluid spectral signature can be generated by the computer 155 based on energy indications from the plural optical filters 302. The display 220 in the surface system 218 can be used to visualize the spectral signature showing signature values with corresponding optical channels.

In one example, the spectral signature can include a formation fluid signature 906 and a mud filtrate signature 908. The fluid composition and fluid properties can be identified based on the spectral signature with corresponding optical channels 904 and signature values 902. Further, with the identified fluid composition and fluid properties, the wellbore operations, such as drilling or wellbore completion, can be effectively performed by identifying locations with greater concentrations of formation fluids.

Figure 10:
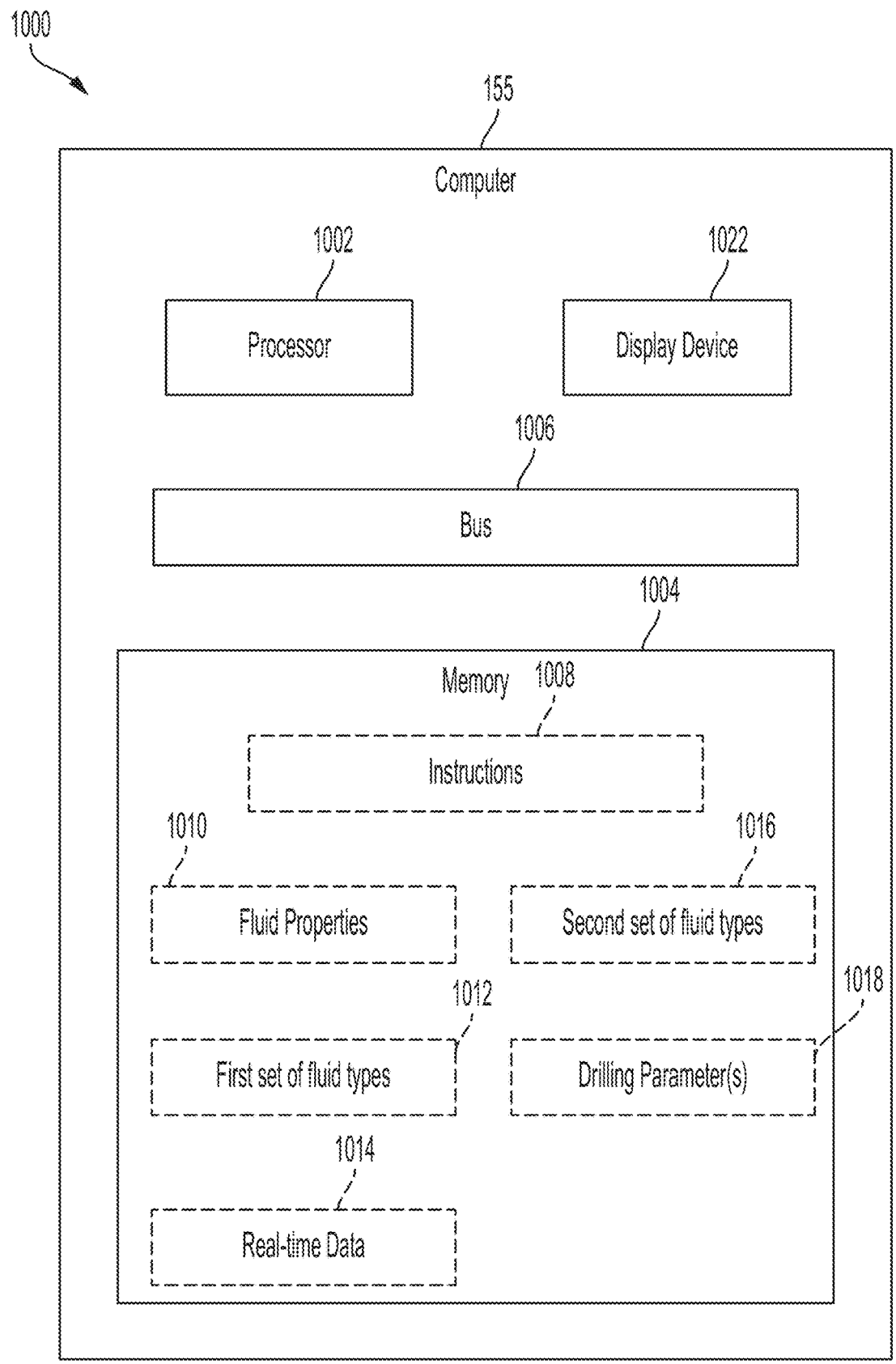
FIG. 10 is a block diagram of an example of a computing device for identifying fluid types for optical channels based on optical measurement according to one example of the present disclosure.

FIG. 10 is a block diagram 1000 of an example of a computer for identifying fluid types for optical channels based on optical measurement according to one example of the present disclosure. The computer 155 can include a processor 1002, a bus 1006, a memory 1004, and a display device 1022. In some examples, the components shown in FIG. 10 can be integrated into a single structure. For example, the components can be within a single housing with a single processing device. In other examples, the components shown in FIG. 10 can be distributed (e.g., in separate housings) and in electrical communication with each other using various processors. It is also possible for the components to be distributed in a cloud computing system or grid computing system.

The processor 1002 can execute one or more operations for determining an operating window. The processor 1002 can execute instructions stored in the memory 1004 to perform the operations. The processor 1002 can include one processing device or multiple processing devices. Non-limiting examples of the processor 1002 include a field-programmable gate array ("FPGA"), an application-specific integrated circuit ("ASIC"), a processor, a microprocessor, etc.

The processor 1002 is communicatively coupled to the memory 1004 via the bus 1006. The memory 1004 may include any type of memory device that retains stored information when powered off. Non-limiting examples of the memory 1004 include electrically erasable and programmable read-only memory ("EEPROM"), flash memory, or any other type of non-volatile memory. In some examples, at least some of the memory 1004 can include a non-transitory medium from which the processor 1002 can read instructions. A computer-readable medium can include electronic, optical, magnetic, or other storage devices capable of providing the processor 1002 with computer-readable instructions or other program code. Non-limiting examples of a computer-readable medium include (but are not limited to) magnetic disk(s), memory chip(s), read-only memory (ROM), random-access memory ("RAM"), an ASIC, a configured processing device, optical storage, or any other medium from which a computer processing device can read instructions. The instructions can include processing device-specific instructions generated by a compiler or an interpreter from code written in any suitable computer-programming language, including, for example, C, C++, C#, etc.

In some examples, the computer 155 includes a display device 1022. The display device 1022 can represent one or more components used to output data. Examples of the display device 1022 can include a liquid-crystal display (LCD), a computer monitor, a touch-screen display, etc.

The computer 155 may log fluid properties 1010 of wellbore within the memory 1004. The computer 155 can determine a first set of fluid types 1012 as identified fluid identification associated with the fluid properties 1010. The first set of fluid types 1012 can correspond composition of formation or mud filtrate within the wellbore, and the computer 155 can use the first set of fluid types 1012 to determine a second set of fluid types 1016.

The computer 155 can adjust drilling parameter(s) 1018 of the drilling operation in real time based on the first set of fluid types 1012 and the second set of fluid types 1016. Examples of the drilling parameter(s) 1018 can include a wellbore pressure, a mud weight, fluid properties, a pump rate, a rate of penetration, a drilling trajectory, or a combination of these. In some examples, the first set of fluid types 1012 and the second set of fluid types 1016 may be considered real-time data 1014 that is available for further processing in real-time or in near real-time. The real-time data 1014 may be processed to identify formation fluids within the wellbore, and the identification of the formation fluids may provide data used to further control the drilling parameter(s) 1018 or other downhole operations (e.g., completion operations).

In some aspects, a system, a method, and a non-transitory computer-readable medium for adjusting parameters of a drilling operation are provided according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a system comprising: a tester tool positionable within a wellbore, the tester tool comprising a plurality of optical filters positionable to detect optical data from within the wellbore; a processing device; and a memory device that includes instructions executable by the processing device for causing the processing device to: identify, by pre-set criteria, a first plurality of optical channels and a second plurality of optical channels using the optical data generated from the plurality of optical filters of the tester tool; determine, from the optical data, a first plurality of fluid types detected by each channel in the first plurality of optical channels using a bootstrap fluid identification technique; determine, from the optical data and the first plurality of fluid types, a second plurality of fluid types detected by each channel in the second plurality of optical channels using a guided fluid identification technique; and generate a spectral signature indicating fluid types for each channel within the tester tool based on the first plurality of fluid types and second plurality of fluid types.

Example 2 is the system of example 1, wherein the instructions are further executable for causing the processing device to: identify a subsurface fluid from a wellbore using the spectral signature.

Example 3 is the system of examples 1-2, wherein the pre-set criteria are used to evaluate sensitivities and stabilities of each channel from the plurality of optical filters using the optical data.

Example 4 is the system of examples 1-3, wherein the optical data comprises optical energy indications for each channel in the first plurality of optical channels and the second plurality of optical channels, wherein the optical energy indications are dependent upon a transmitting spectrum and a plurality of transfer functions of the plurality of optical filters associated with the first plurality of optical channels and the second plurality of optical channels.

Example 5 is the system of example 4, wherein the bootstrap fluid identification technique comprises: clustering the optical data for each channel in the first plurality of optical channels into at least two groups based on the optical energy indications of the optical data; and labeling each group of the at least two groups with one of at least two fluid types for each channel in the first plurality of optical channels based on the optical energy indications of the optical data.

Example 6 is the system of example 4, wherein the guided fluid identification technique comprises: calculating at least one stationary statistic from the first plurality of fluid types; clustering the optical data for each channel in the second plurality of optical channels into at least two groups based on the optical energy indications of the optical data; and labeling each group of the at least two groups with one of at least two fluid types for each channel in the second plurality of optical channels based on the at least one stationary statistic.

Example 7 is the system of example 6, wherein the at least one stationary statistic comprises an accumulated formation fluid ratio.

Example 8 is the system of examples 1-7, wherein the guided fluid identification technique comprises a prediction of a subsurface fluid composition within the wellbore.

Example 9 is the system of examples 1-8, wherein the plurality of optical filters comprises a dual-ring configuration.

Example 10 is a method comprising: identifying, by pre-set criteria, a first plurality of optical channels and a second plurality of optical channels using optical data generated from a plurality of optical filters of a tester tool;

determining, from the optical data, a first plurality of fluid types detected by each channel in the first plurality of optical channels using a bootstrap fluid identification technique; determining, from the optical data and the first plurality of fluid types, a second plurality of fluid types detected by each channel in the second plurality of optical channels using a guided fluid identification technique; and generating a spectral signature indicating fluid types for each channel within the tester tool based on the first plurality of fluid types and second plurality of fluid types.

Example 11 is the method of example 10, wherein the pre-set criteria are used to evaluate sensitivities and stabilities of each channel from the plurality of optical filters using the optical data.

Example 12 is the method of examples 10-11, wherein the optical data comprises optical energy indications for each channel in the first plurality of optical channels and the second plurality of optical channels, wherein the optical energy indications are dependent upon a transmitting spectrum and a plurality of transfer functions of the plurality of optical filters associated with the first plurality of optical channels and the second plurality of optical channels.

Example 13 is the method of example 12, wherein the bootstrap fluid identification technique comprises: clustering the optical data for each channel in the first plurality of optical channels into at least two groups based on the optical energy indications of the optical data; and labeling each group of the at least two groups with one of at least two fluid types for each channel in the first plurality of optical channels based on the optical energy indications of the optical data.

Example 14 is the method of example 12, wherein the guided fluid identification technique comprises: calculating at least one stationary statistic from the first plurality of fluid types; clustering the optical data for each channel in the second plurality of optical channels into at least two groups based on the optical energy indications of the optical data; and labeling each group of the at least two groups with one of at least two fluid types for each channel in the second plurality of optical channels based on the at least one stationary statistic.

Example 15 is the method of example 14, wherein the at least one stationary statistic comprises an accumulated formation fluid ratio.

Example 16 is a non-transitory computer-readable medium comprising instructions that are executable by a processing device for causing the processing device to perform operations comprising: identifying, by pre-set criteria, a first plurality of optical channels and a second plurality of optical channels using an optical data generated from a plurality of optical filters of a tester tool; determining, from the optical data, a first plurality of fluid types detected by each channel in the first plurality of optical channels using a bootstrap fluid identification technique; determining, from the optical data and the first plurality of fluid types, a second plurality of fluid types detected by each channel in the second plurality of optical channels using a guided fluid identification technique; and generating a spectral signature indicating fluid types for each channel within the tester tool based on the first plurality of fluid types and second plurality of fluid types.

Example 17 is the non-transitory computer-readable medium of example 16, wherein the optical data comprises optical energy indications for each channel in the first plurality of optical channels and the second plurality of optical channels, wherein the optical energy indications are dependent upon a transmitting spectrum and a plurality of transfer functions of the plurality of optical filters associated with the first plurality of optical channels and the second plurality of optical channels.

Example 18 is the non-transitory computer-readable medium of example 17, wherein the bootstrap fluid identification technique comprises: clustering the optical data for each channel in the first plurality of optical channels into at least two groups based on the optical energy indications of the optical data; and labeling each group of the at least two groups with one of at least two fluid types for each channel in the first plurality of optical channels based on the optical energy indications of the optical data.

Example 19 is the non-transitory computer-readable medium of example 17, wherein the guided fluid identification technique comprises: calculating at least one stationary statistic from the first plurality of fluid types; clustering the optical data for each channel in the second plurality of optical channels into at least two groups based on the optical energy indications of the optical data; and labeling each group of the at least two groups with one of at least two fluid types for each channel in the second plurality of optical channels based on the at least one stationary statistic.

Example 20 is the non-transitory computer-readable medium of examples 16-19, wherein the plurality of optical filters comprises a dual-ring configuration.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system comprising:
a tester tool positionable within a wellbore, the tester tool comprising a plurality of optical filters positionable to detect optical data from within the wellbore;
a processing device; and
a memory device that includes instructions executable by the processing device for causing the processing device to:
identify, by pre-set criteria, a first plurality of optical channels and a second plurality of optical channels using the optical data generated from the plurality of optical filters of the tester tool;
determine, from the optical data, a first plurality of fluid types detected by each channel in the first plurality of optical channels using a bootstrap fluid identification technique;
determine, from the optical data and the first plurality of fluid types, a second plurality of fluid types detected by each channel in the second plurality of optical channels using a guided fluid identification technique; and
generate a spectral signature indicating fluid types for each channel within the tester tool based on the first plurality of fluid types and second plurality of fluid types.

2. The system of claim 1, wherein the instructions are further executable for causing the processing device to:
identify a subsurface fluid from a wellbore using the spectral signature.

3. The system of claim 1, wherein the pre-set criteria are used to evaluate sensitivities and stabilities of each channel from the plurality of optical filters using the optical data.

4. The system of claim 1, wherein the optical data comprises optical energy indications for each channel in the first plurality of optical channels and the second plurality of optical channels, wherein the optical energy indications are dependent upon a transmitting spectrum and a plurality of transfer functions of the plurality of optical filters associated with the first plurality of optical channels and the second plurality of optical channels.

5. The system of claim 4, wherein the bootstrap fluid identification technique comprises:
clustering the optical data for each channel in the first plurality of optical channels into at least two groups based on the optical energy indications of the optical data; and
labeling each group of the at least two groups with one of at least two fluid types for each channel in the first plurality of optical channels based on the optical energy indications of the optical data.

6. The system of claim 4, wherein the guided fluid identification technique comprises:
calculating at least one stationary statistic from the first plurality of fluid types;
clustering the optical data for each channel in the second plurality of optical channels into at least two groups based on the optical energy indications of the optical data; and
labeling each group of the at least two groups with one of at least two fluid types for each channel in the second plurality of optical channels based on the at least one stationary statistic.

7. The system of claim 6, wherein the at least one stationary statistic comprises an accumulated formation fluid ratio.

8. The system of claim 1, wherein the guided fluid identification technique comprises a prediction of a subsurface fluid composition within the wellbore.

9. The system of claim 1, wherein the plurality of optical filters comprises a dual-ring configuration.

10. A method comprising:
identifying, by pre-set criteria, a first plurality of optical channels and a second plurality of optical channels using optical data generated from a plurality of optical filters of a tester tool;
determining, from the optical data, a first plurality of fluid types detected by each channel in the first plurality of optical channels using a bootstrap fluid identification technique;
determining, from the optical data and the first plurality of fluid types, a second plurality of fluid types detected by each channel in the second plurality of optical channels using a guided fluid identification technique; and
generating a spectral signature indicating fluid types for each channel within the tester tool based on the first plurality of fluid types and second plurality of fluid types.

11. The method of claim 10, wherein the pre-set criteria are used to evaluate sensitivities and stabilities of each channel from the plurality of optical filters using the optical data.

12. The method of claim 10, wherein the optical data comprises optical energy indications for each channel in the first plurality of optical channels and the second plurality of optical channels, wherein the optical energy indications are dependent upon a transmitting spectrum and a plurality of transfer functions of the plurality of optical filters associated with the first plurality of optical channels and the second plurality of optical channels.

13. The method of claim 12, wherein the bootstrap fluid identification technique comprises:
clustering the optical data for each channel in the first plurality of optical channels into at least two groups based on the optical energy indications of the optical data; and
labeling each group of the at least two groups with one of at least two fluid types for each channel in the first plurality of optical channels based on the optical energy indications of the optical data.

14. The method of claim 12, wherein the guided fluid identification technique comprises:
calculating at least one stationary statistic from the first plurality of fluid types;
clustering the optical data for each channel in the second plurality of optical channels into at least two groups based on the optical energy indications of the optical data; and
labeling each group of the at least two groups with one of at least two fluid types for each channel in the second plurality of optical channels based on the at least one stationary statistic.

15. The method of claim 14, wherein the at least one stationary statistic comprises an accumulated formation fluid ratio.

16. A non-transitory computer-readable medium comprising instructions that are executable by a processing device for causing the processing device to perform operations comprising:
identifying, by pre-set criteria, a first plurality of optical channels and a second plurality of optical channels using an optical data generated from a plurality of optical filters of a tester tool;
determining, from the optical data, a first plurality of fluid types detected by each channel in the first plurality of optical channels using a bootstrap fluid identification technique;
determining, from the optical data and the first plurality of fluid types, a second plurality of fluid types detected by each channel in the second plurality of optical channels using a guided fluid identification technique; and
generating a spectral signature indicating fluid types for each channel within the tester tool based on the first plurality of fluid types and second plurality of fluid types.

17. The non-transitory computer-readable medium of claim 16, wherein the optical data comprises optical energy indications for each channel in the first plurality of optical channels and the second plurality of optical channels, wherein the optical energy indications are dependent upon a transmitting spectrum and a plurality of transfer functions of the plurality of optical filters associated with the first plurality of optical channels and the second plurality of optical channels.

18. The non-transitory computer-readable medium of claim 17, wherein the bootstrap fluid identification technique comprises:
clustering the optical data for each channel in the first plurality of optical channels into at least two groups based on the optical energy indications of the optical data; and
labeling each group of the at least two groups with one of at least two fluid types for each channel in the first plurality of optical channels based on the optical energy indications of the optical data.

19. The non-transitory computer-readable medium of claim 17, wherein the guided fluid identification technique comprises:

calculating at least one stationary statistic from the first plurality of fluid types;

clustering the optical data for each channel in the second plurality of optical channels into at least two groups based on the optical energy indications of the optical data; and labeling each group of the at least two groups with one of at least two fluid types for each channel in the second plurality of optical channels based on the at least one stationary statistic.

20. The non-transitory computer-readable medium of claim 16, wherein the plurality of optical filters comprises a dual-ring configuration.

* * * * *